(12) United States Patent
Wang et al.

(10) Patent No.: US 9,297,001 B2
(45) Date of Patent: Mar. 29, 2016

(54) PREPARATION METHOD CONDUCIVE TO ENHANCING ENZYMATIC ACTIVITY OF CELLULASE

(71) Applicant: INSTITUTE OF NUCLEAR ENERGY RESEARCH, ATOMIC ENERGY COUNCIL, EXECUTIVE YUAN, Longtan Township (TW)

(72) Inventors: Chun-An Wang, New Taipei (TW); Sheng-Hsin Chou, Longtan Township (TW); Gia-Luen Guo, New Taipei (TW)

(73) Assignee: INSTITUTE OF NUCLEAR ENERGY RESEARCH, ATOMIC ENERGY COUNCIL, EXECUTIVE YUAN (TW)

( * ) Notice: Subject to any disclaimer, the term of this patent is extended or adjusted under 35 U.S.C. 154(b) by 79 days.

(21) Appl. No.: 14/471,080

(22) Filed: Aug. 28, 2014

(65) Prior Publication Data

US 2015/0118717 A1    Apr. 30, 2015

(51) Int. Cl.
*C12N 9/42* (2006.01)
*C12P 39/00* (2006.01)
*C12P 21/00* (2006.01)
*C12R 1/885* (2006.01)
*C12R 1/685* (2006.01)

(52) U.S. Cl.
CPC .............. *C12N 9/2437* (2013.01); *C12P 21/00* (2013.01); *C12P 39/00* (2013.01); *C12R 1/685* (2013.01); *C12R 1/885* (2013.01); *Y02P 20/52* (2015.11)

(58) Field of Classification Search
None
See application file for complete search history.

(56) References Cited

U.S. PATENT DOCUMENTS

2008/0138872 A1* 6/2008 Smith ........................ C12P 7/10
435/165

OTHER PUBLICATIONS

Liu, Hui-Qin; Feng, Yue; Zhao, Dan-Qing; Jiang, Jian-Xin "Evaluation of cellulases produced from four fungi cultured on furfural residues and microcrystalline cellulose" Biodegradation, 2012, 23, pp. 465-472, DOI 10.1007/s10532-011-9525-6.*
Ahamed, Aftab; Vermette, Patrick "Enhanced enzyme production from mixed cultures of Trichoderma reesei RUT-C30 and Aspergillus niger LMA grown as fed batch in a stirred tank bioreactor" Biochem. Eng. J., Oct. 2008, 42(1), p. 41-46, doi:10.1016/j.bej.2008.05.007.*
ATCC Products Genreal information "Trichoderma reesei Simmons (ATCC 56765)", <URL: http://www.atcc.org/products/all/56765.aspx>, accessed online Jan. 2, 2015, 1 page.*

(Continued)

*Primary Examiner* — Thane Underdahl
*Assistant Examiner* — Aaron J Kosar
(74) *Attorney, Agent, or Firm* — Schmeiser, Olsen & Watts, LLP

(57) ABSTRACT

A preparation method conducive to enhancing enzymatic activity of cellulase includes the steps of preparing a first inducer, preparing preculture hyphae, producing enzymes by a single strain, feeding a second inducer, and producing enzymes by co-culture strains. Main ingredients of the first inducer and the second inducer are cellulose and lactose, respectively. The enzymatic activity of the cellulase produced is enhanced by induction of cellulose and lactose and co-culture of *Trichoderma* and *Aspergillus*.

11 Claims, 1 Drawing Sheet

(56) References Cited

OTHER PUBLICATIONS

Figure 1:
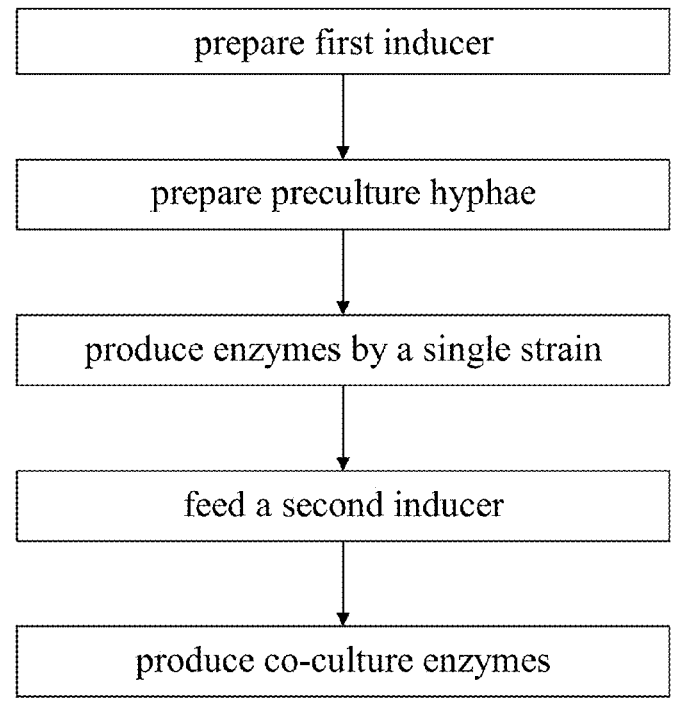

ATCC Products Genreal information "Aspergillus niger van Tieghem (ATCC 10864)", <URL: http://www.atcc.org/Products/All/10864.aspx#generalinformation>, accessed online Jan. 2, 2015, 1page.*

Global Catalogue of Microorganisms, Strain Nos. BCRC31494 and BCRC32924, Accessed online Jan. 2, 2015, <URL: http://gcm.wfcc.info/Strain_numberToInfoServlet?strain_number=BCRC%2032494> and <~BCRC%2032924>, 2 pages.*

* cited by examiner

PREPARATION METHOD CONDUCIVE TO ENHANCING ENZYMATIC ACTIVITY OF CELLULASE

CROSS-REFERENCE TO RELATED APPLICATION

This non-provisional application claims priority under 35 U.S.C. §119(a) on Patent Application No(s).102139476 filed in Taiwan, R.O.C. on Oct. 31, 2013, the entire contents of which are hereby incorporated by reference.

FIELD OF TECHNOLOGY

The present invention relates to methods of preparing cellulase, and more particularly, to a preparation method conducive to enhancing enzymatic activity of cellulase by co-culture strains of *Trichoderma* and *Aspergillus*.

BACKGROUND

Cellulose is a large polysaccharide which comprises D-glucose formed by $\beta$-1,4-glucanase and is the main ingredient of a plant cell wall. Cellulose is a natural polymer which exists in great quantities on the Earth, and its carbon content accounts for more than 50% of the carbon content of the plant kingdom. Plants make use of the carbon dioxide in the air by photosynthesis, and then store the chemical energy of carbon dioxide in the bonds of cellulose molecules. Hence, the effective decomposition of cellulose and conversion of its energy and carbon source into energy accessible to human beings will provide a solution to the current food crisis and energy crisis facing humankind nowadays.

Conventional methods for use in processing cellulose fall into three categories, namely chemical processing, physical processing, and cellulase-based decomposition. Cellulase is a composite enzyme composed of multiple hydrolases, and it is produced by fungi, bacteria, and actinomyces in nature. Insoluble cellulose is usually decomposed into monosaccharides for use as a carbon source during a biotech manufacturing process. Cellulase, which degrades cellulose, is available in three types and functions according to its enzyme commission (EC) number as follows: (1) endo-cellulose hydrolase (EC 3.2.1.4; endo-$\beta$-1,4-glucanase) cuts the $\beta$-1,4 glucanase in the cellulose molecule at random and releases cello-oligosaccharides to thereby increase the number of reducing ends and decreasing viscosity; (2) exo-cellulose hydrolase (EC 3.2.1.91; exo-$\beta$-1,4-glucanase) cuts cellobiose from the highly crystallized terminal end of cellulose; and (3) EC 3.2.1.21; $\beta$-1,4-glucosidase hydrolyzes cellobiose to produce glucose.

The enzymatic activity of exo-cellulose hydrolase is inhibited by the feedback from its product—cello-disaccharides, and the presence of $\beta$-1,4-glucosidase is conducive to the prevention of excessive accumulation of cello-disaccharides and thus the reduction in its feedback inhibition of exo-cellulose hydrolase.

Conventional commercially available cellulases are produced mostly by *Trichoderma* species or *Aspergillus* species. Although *Trichoderma* secretes a huge amount of end-cellulose hydrolase and exo-cellulose hydrolase, its $\beta$-1,4-glucosidase demonstrates relatively low enzymatic activity and thus is likely to cause the accumulation of cello-disaccharides produced during the process of enzyme-based hydrolysis of fibrous biological matters, thereby bringing about feedback inhibition and thus deteriorated efficacy of hydrolysis. As a result, it is necessary to overcome the aforesaid drawbacks by including the $\beta$-1,4-glucosidase produced by *Aspergillus*.

Accordingly, it is imperative to perform co-cultivation on two different strains, namely *Trichoderma* and *Aspergillus* so as to produce their cellulases by induction of cellulose and lactose and thus enhance the enzymatic activities of their cellulases.

SUMMARY

It is an objective of the present invention to produce cellulase by co-culture strains of fungi with a view to overcoming a drawback of the prior art, that is, the overly low enzymatic activity of the cellulase produced by a single strain.

In order to achieve the above and other objectives, the present invention provides a preparation method conducive to enhancing enzymatic activity of cellulase. The preparation method comprises steps of: preparing a first inducer by treating a raw material for cellulose production with a diluted acid; preparing a preculture hyphae by inoculating two preculture media with *Trichoderma* spores and *Aspergillus* spores, respectively, followed by allowing the inoculated preculture media to sit for 48 hours and 24 hours, respectively; producing enzymes by a single strain by mixing the first inducer and a medium in a fermentation tank, inoculating the medium in the fermentation tank with *Trichoderma* preculture hyphae, followed by allowing the inoculated medium to sit for 24 to 60 hours; feeding a second inducer by feeding the second inducer to the fermentation tank continuously, wherein a main ingredient of the second inducer is lactose; and producing co-culture enzymes by inoculating the medium in the fermentation tank with *Aspergillus* preculture hyphae, followed by allowing the inoculated medium in the fermentation tank to sit for 96 to 192 hours in total.

Regarding the aforesaid method, the raw material for cellulose production is a straw.

Regarding the aforesaid method, the first inducer is prepared by crushing a straw physically, mixing the crushed straw with a diluted acid to destroy a structure of the straw, and steaming the straw at 150-200° C. for 20-40 minutes.

Regarding the aforesaid method, the pre-medium comprises a glucose of 0.5% w/w to 2% w/w.

Regarding the aforesaid method, the lactose in the second inducer is of a concentration of 150 g/L to 300 g/L.

Regarding the aforesaid method, preferably, the co-culture enzyme is produced by inoculating the medium with *Trichoderma* preculture hyphae, allowing the inoculated medium to sit for 48 hours, and inoculating the medium in the fermentation tank with *Aspergillus* preculture hyphae.

Regarding the aforesaid method, preferably, from the $24^{th}$ hour of the cultivation process, the second inducer is fed to the fermentation tank every 5 minutes, and the feeding process takes 96 hours.

Regarding the aforesaid method, preferably, upon completion of a final feed of the second inducer, a total volume of the second inducer accounts for 33% of that of substances contained in the fermentation tank, and a volume of each feed of the second inducer equals 0.0868% of the initial total volume of the second inducer.

According to the present invention, a preparation method conducive to enhancing enzymatic activity of cellulase is advantageously characterized in that: the achieved overall enzymatic activity is 21.7 FPU/ml which is 3.6 times higher than the enzymatic activity of *Trichoderma* (6 FPU/ml) produced alone and 6.3 times higher than the enzymatic activity of *Aspergillus* (3.4 FPU/ml) produced alone, thereby indicating that the overall enzymatic activity yielded by the preparation method conducive to enhancing enzymatic activity of cellulase according to the present invention is significantly higher than the overall enzymatic activity yielded by the method of producing enzymes by a single strain.

BRIEF DESCRIPTION

Figure 2:
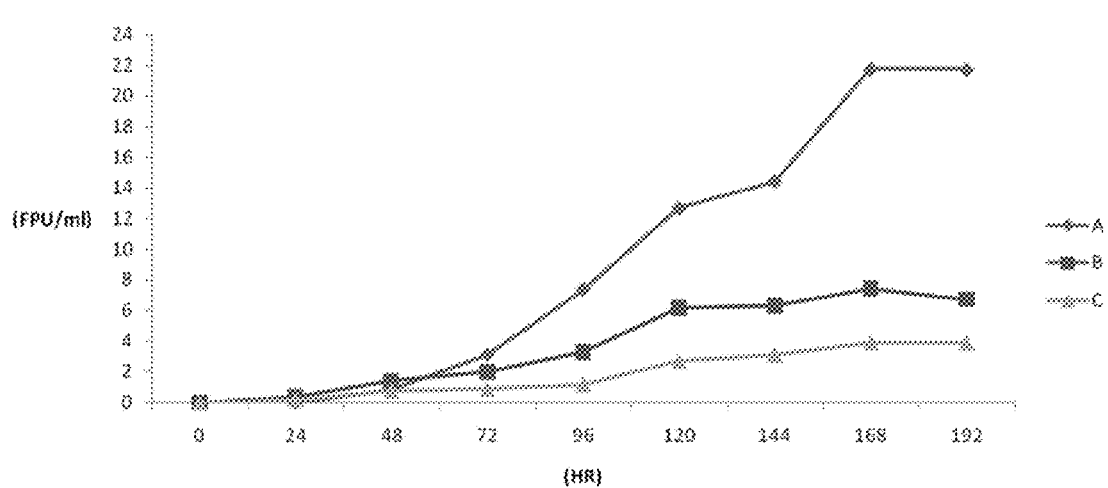

FIG. 1 is a flow chart of a preparation method conducive to enhancing enzymatic activity of cellulase according to the present invention; and FIG. 2 is a schematic view of the analysis of the overall enzymatic activity of cellulase according an embodiment of the present invention.

DETAILED DESCRIPTION

Embodiment 1

Method of Producing Co-Culture Cellulase

Referring to FIG. 1, there is shown a preparation method conducive to enhancing enzymatic activity of cellulase according to the present invention. A first inducer is prepared by cutting a straw to a length of 2cm to 5cm, mixing the cut straw with 3% w/w sulfuric acid by a screw extruder, and conveying the mixture to a high-temperature environment in which the mixture is steamed at 150° C. for 25 minutes to destroy the structure of the straw, so as to prepare the first inducer.

A preculture hyphae is prepared as follows: a preculture medium is prepared; the preculture medium contains 1.5% glucose and ingredients shown in Table 1 (barring glucose, the ingredients shown in Table 1 are ingredients of a conventional medium); the pH of the preculture medium is adjusted to be 5.0; the preculture medium undergoes high-pressure sterilization at 121° C. for 20 minutes; and the sterilized preculture medium is cooled down to room temperature. Afterward, the preculture medium is inoculated with *Trichoderma* spores of *Trichoderma reesei* RUT-C30 BCRC32924, wherein the *Trichoderma* spores are of a concentration of 1×106/mL, and then the inoculated preculture medium sits at 30° C., at 150 rpm, and for 48 hours, so as to produce *Trichoderma* preculture hyphae. Another preculture medium with the aforesaid ingredients is inoculated with *Aspergillus* spores of *Aspergillus niger* BCRC31494, wherein the *Aspergillus* spores are of a concentration of 1×106/mL, and then the inoculated preculture medium sits at 30° C., at 150 rpm, and for 24 hours, so as to produce *Aspergillus* preculture hyphae.

TABLE 1

| Component | Content (g/L) |
|---|---|
| peptone | 1.0 |
| urea | 0.3 |
| $(NH_4)_2SO_4$ | 1.4 |
| $KH_2PO_4$ | 2.0 |
| $CaCl_2$ | 0.3 |
| $MgSO_4 \cdot 7H_2O$ | 0.3 |
| $FeSO_4 \cdot 7H_2O$ | 0.005 |
| $ZnSO_4 \cdot 7H_2O$ | 0.0014 |
| $MnSO_4 \cdot 4H_2O$ | 0.0016 |
| $CoCl_2 \cdot 6H_2O$ | 0.0037 |

The step of producing enzymes by a single strain is as follows. A medium with the ingredients shown in Table 1 is prepared. A first inducer is fed to the medium until the solid to liquid ratio of the mixture is 4%. Then, adjust the pH of the medium to 5.0. Afterward, the medium undergoes high-pressure sterilization at 121° C. for 20 minutes. Then the sterilized medium is introduced into a 5 L fermentation tank. Eventually, the sterilized medium in the fermentation tank is inoculated with *Trichoderma* preculture hyphae produced in the preceding step in a manner that the volume of the *Trichoderma* preculture hyphae equals one-tenth of the medium in the fermentation tank. The inoculated medium sits at 30° C., pH 5.0, with 23% dissolved oxygen, and for 48 hours.

The step of feeding the second inducer is as follows. A second inducer with lactose as its main ingredient is prepared, such that the second inducer is composed of ingredients shown in Table 2, wherein the lactose is of a concentration of 200 g/L. Barring lactose, the ingredients shown in Table 2 are those of a conventional medium, however, since the volume of the second inducer equals 33% of the volume of the substances in the fermentation tank, the concentrations of the ingredients of the second inducer are adjusted to be higher than those of the ingredients of a conventional medium, such that the resultant medium is similar to the conventional medium in concentration. From the 24th hour of the cultivation process, the second inducer is fed to the fermentation tank every 5 minutes, and the feeding process takes 96 hours. Upon completion of a final feed of the second inducer, a total volume of the second inducer accounts for 33% of that of substances contained in the fermentation tank, and a volume of each feed of the second inducer equals 0.0868% of the initial total volume of the second inducer.

TABLE 2

| Component | Content (g/L) |
|---|---|
| peptone | 2.5 |
| urea | 0.75 |
| $(NH_4)_2SO_4$ | 3.5 |
| $KH_2PO_4$ | 5.0 |
| $CaCl_2$ | 0.75 |
| $MgSO_4 \cdot 7H_2O$ | 0.75 |
| $FeSO_4 \cdot 7H_2O$ | 0.025 |
| $ZnSO_4 \cdot 7H_2O$ | 0.007 |
| $MnSO_4 \cdot 4H_2O$ | 0.008 |
| $CoCl_2 \cdot 6H_2O$ | 0.0185 |
| lactose | 150-300 |

As regard the production of co-culture enzymes, it begins 48 hours after the inoculation of the *Trichoderma* preculture hyphae. The medium in the fermentation tank is inoculated with the *Aspergillus* preculture hyphae previously produced in the preculture hyphae preparation step. The volume of the *Aspergillus* preculture hyphae equals one-tenth of the volume of the medium in the fermentation tank. The inoculated medium in the fermentation tank sits at 30° C., pH 5.0, with 23% dissolved oxygen, and for 144 hours, so as to produce cellulase.

During the aforesaid preparation and production processes, the enzymatic activity of cellulase varies. During the process of inoculation of the *Trichoderma* preculture hyphae and the process of extraction of contents from the fermentation tank every 24 hours, the crude extracts of cellulase, which are obtained by solid-liquid separation, undergo enzymatic activity analysis.

As regards the enzymatic activity analysis of the crude extracts, the crude extracts are obtained by means of the cellulase production process and then undergo the enzymatic activity analysis with a related technique put forth by the International Union of Pure and Applied Chemistry (IUPAC). The overall enzymatic activity of cellulase is tested by a filter paper, that is, Whatman No.1 filter paper, and then the crude extracts undergo enzyme-based hydrolysis to produce a reducing sugar and a coloring agent 3,5-dinitrosalicylic acid (DNS) before undergoing quantitative analysis with enhanced absorbance of 540 nm. The overall enzymatic activity of the cellulase is evaluated by a 50 mg Whatman No. 1 filter paper, at 50° C. and for 60 minutes to produce 2.0 mg of reducing sugar, with FPU being the enzymatic activity unit, and is defined as being subjected to related analysis requirements, releasing 0.37 μmol of reducing sugar per minute, at 1 unit/ml.

As regards the co-culture cellulase production method in embodiment 1, curve A in FIG. 2 depicts the result of the evaluation of the enzymatic activity against time, where x-axis indicates the total cultivation duration (hour) from the inoculation of Trichoderma preculture hyphae, and y-axis indicates the overall enzymatic activity of cellulase in FPU/ml, wherein the overall enzymatic activity of cellulase is 21.7 FPU/ml at the end of 192 hours of cultivation.

Embodiment 2

Producing Cellulase by a Single Strain

To compare and contrast the co-culture cellulase production method of embodiment 1 and the method of producing cellulase by a single strain, the following description is about producing cellulase with Trichoderma and producing cellulase with Aspergillus to evaluate the overall enzymatic activity at different points in time. The following description omits the inoculation of the second strain. The method of producing cellulase by a single strain of embodiment 2 is identical to the co-culture production method of embodiment 1 in terms of the steps of producing cellulase by a single strain, the preculture hyphae inoculation amount, ingredients of a medium and the second inducer, the feeding technique, related parameters placed under control, and the technique of evaluating the overall enzymatic activity of cellulase every 24 hour.

The result of the evaluation of producing Trichoderma by a single strain is depicted with curve B in FIG. 2, and the result of the evaluation of producing Aspergillus by a single strain is depicted with curve C in FIG. 2.

Referring to FIG. 2, the overall enzymatic activity of 21.7 FPU/ml detected at the $96^{th}$ hour using the co-culture production method is significantly higher than the overall enzymatic activity of 6 FPU/ml detected at the $192^{th}$ hour using the method of producing Trichoderma by a single strain as well as the overall enzymatic activity of 3.4 FPU/ml detected at the $192^{th}$ hour using the method of producing Trichoderma by a single strain, thereby indicating that the overall enzymatic activity yielded by the co-culture production method is 3.6 times and 6.3 times higher than the overall enzymatic activities yielded by the method of producing enzymes by a single strain, respectively.

Embodiment 3

Evaluating the Time Intervals at which Inoculation takes Place

The effects of the timing of Aspergillus inoculation on overall enzymatic activity are described below. With the production method of embodiment 1, the adjustment of the time intervals at which inoculation takes place is performed by conducting three different tests, wherein three instances of inoculation of the Aspergillus preculture hyphae occur 24 hours, 36 hours, and 60 hours after the inoculation of the Trichoderma preculture hyphae, respectively, and then the cultivation of the Aspergillus preculture hyphae stops at the end of the $192^{th}$ hour from the commencement of the inoculation of the Trichoderma preculture hyphae. The evaluation of the time intervals at which inoculation takes place in embodiment 3 employs the overall enzymatic activity evaluation technique of embodiment 1 to evaluate the overall enzymatic activity at the end of the $192^{th}$ hour from the commencement of the inoculation of the Trichoderma preculture hyphae. In embodiment 3, the identified effects of the timing of Aspergillus inoculation on overall enzymatic activity are described in Table 3.

TABLE 3

| Time intervals at which inoculations of Trichoderma and Aspergillus take place (hour) | Overall enzymatic activity of cellulase (FPU/ml) |
| --- | --- |
| 24 | 12 |
| 36 | 17.5 |
| 48 | 21.7 |
| 60 | 14.26 |

As shown in Table 3, the overall enzymatic activities of Trichoderma and Aspergillus produced at the $192^{th}$ hour by the co-culture production method in embodiment 3 are significantly higher than the overall enzymatic activity (6 FPU/ml) of Trichoderma produced alone in embodiment 2 and the overall enzymatic activity (3.4 FPU/ml) of Aspergillus produced alone in embodiment 2, wherein the overall enzymatic activities of Trichoderma and Aspergillus produced at the $192^{th}$ hour by the co-culture production method in embodiment 3 peak at 21.7 FPU/ml with a time interval of 48 hours.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A preparation method conducive to enhancing enzymatic activity of cellulase, the preparation method comprising steps of:
   preparing a first inducer by treating a raw material for cellulose production with a diluted acid;
   preparing a preculture hyphae by inoculating two preculture media comprising:
      inoculating the first preculture media with Trichoderma spores of Trichoderma reesei RUT-C30 BCBRC 32924 and the second preculture media with Aspergillus spores of Aspergillus niger BCRC31494, followed by
      (ii) allowing the first and second inoculated preculture media to sit for 48 hours and 24 hours, respectively, thereby forming a first Trichoderma preculture and a second Aspergillus preculture;
   (c) producing cellulase with Trichoderma preculture by a single strain by:
      (i) mixing the first induce and a fermentation medium in a fermentation tank,
      (ii) inoculating the fermentation medium in the fermentation tank with the first Trichoderma preculture, followed by
      (iii) cultivating for a period of 24 to 60 hours, thereby producing said cellulase;
   (d) feeding a second inducer to the fermentation tank continuously, wherein a main ingredient of the second inducer is lactose; and (e) inoculating the medium in the fermenation tank which comprises *Trichoderma* with second *Aspergillus* preculture, then allowing this inoculated co-culture of *Trichoderma* and *Aspergillus* in fermentation tank to cultivate for 96 to 192 hours in total, to accumulate additional cellulase in the medium, wherein the inoculation of the second *Aspergillus* preculture is performed 24 to 60 hours after the first *Trichoderma* preculture was inoculated into the fermentation tank.

2. The preparation method of claim 1, wherein the raw material for cellulose production is a straw.

3. The preparation method of claim 2, wherein the first inducer is prepared by crushing said straw physically, mixing the crushed straw with a diluted acid to destroy a structure of the straw, and steaming the straw at 150-200° C. for 20-40 minutes.

4. The preparation method of claim 1, wherein the first and second preculture media comprise glucose in an amount of 0.5% w/w to 2% w/w.

5. The preparation method of claim 1, wherein the lactose in the second inducer is of a concentration of 150 g/L to 300 g/L.

6. The preparation method of claim 1, wherein the first *Trichoderma* preculture is cultivated for 48 hours in the fermentation tank before the second *Aspergillus* preculture is inoculated into the fermentation tank.

7. The preparation method of claim 6, wherein the feeding of the second inducer comprises, after cultivating the *Trichoderma* in the fermentation tank for $24^{th}$ hours feeding the second inducer to the fermentation tank every 5 minutes for a period of 96 hours.

8. The preparation method of claim 7, wherein, upon completion of a final feed of the second inducer, the second inducer accounts for 33% of the total of substances contained in the fermentation tank.

9. The preparation method of claim 1, wherein the feeding of the second inducer comprises, after cultivating the *Trichoderma* in the fermentation tank for $24^{th}$ hours, feeding the second inducer to the fermenation tank every 5 minutes for a period of 96 hours.

10. The preparation method of claim 9, wherein, upon completion of a final feed of the second inducer, the second inducer accounts for 33% of the total volume of substances contained in the fermentation tank.

11. The preparation method of claim 1, wherein said period of 24 to 60 hours in step (c) (iii) is a period of 48 hours.

\* \* \* \* \*